United States Patent [19]

Schalkowsky et al.

[11] Patent Number: 5,547,872
[45] Date of Patent: Aug. 20, 1996

[54] METHOD AND APPARATUS FOR CLEANING THE SAMPLE DELIVERY STYLUS OF MICROPROCESSOR CONTROLLED SPIRAL PLATERS

[75] Inventors: Samuel Schalkowsky, Chevy Chase; Frances M. Scher, Gaithersburg, both of Md.

[73] Assignee: Spiral Biotech, Inc., Bethesda, Md.

[21] Appl. No.: 386,669

[22] Filed: Feb. 10, 1995

[51] Int. Cl.⁶ .................................................. G01N 35/02
[52] U.S. Cl. ......................... 436/49; 436/43; 436/50; 436/54; 436/55; 422/63; 422/64; 422/67; 435/286.1; 435/286.3; 435/286.4; 435/286.5; 435/287.3; 435/293.2; 435/309.1
[58] Field of Search .................. 436/43, 45, 49, 436/50, 54, 55; 422/63, 64, 67, 72; 435/287, 289, 292, 293, 294, 295, 299, 312, 809, 283.1, 286.1, 286.3, 286.4, 286.5, 287.3, 293.2, 309.1, 309.2, 309.4

[56] References Cited

U.S. PATENT DOCUMENTS

| | | | |
|---|---|---|---|
| 3,799,844 | 3/1974 | Campbell et al. | 435/292 |
| 3,892,632 | 7/1975 | Campbell et al. | 435/293 X |
| 4,343,766 | 8/1982 | Sisti et al. | 422/63 |
| 4,456,037 | 6/1984 | Gocho | 422/100 X |
| 4,514,495 | 4/1985 | Schalkowsky et al. | 435/292 X |
| 4,517,292 | 5/1985 | Schalkowsky et al. | 435/292 X |
| 4,543,238 | 9/1985 | Mimura et al. | 422/63 |
| 4,730,631 | 3/1988 | Schwartz | 422/63 X |
| 5,246,837 | 9/1993 | Schalkowsky | 435/29 |
| 5,279,794 | 1/1994 | Sasao | 422/100 |
| 5,429,944 | 7/1995 | Schalkowsky | 435/292 |

FOREIGN PATENT DOCUMENTS 9324609  12/1993  WIPO.

OTHER PUBLICATIONS

Autoplate™ Brochure published 1994.
Autoplate™ Model 3000 User Guide, (Copyright 1994).

*Primary Examiner*—Jill Warden
*Assistant Examiner*—Maureen M. Wallenhorst
*Attorney, Agent, or Firm*—Antonelli, Terry, Stout & Kraus

[57] ABSTRACT

A method and apparatus for cleaning the sample delivery stylus tubing of spiral platers to prevent the carry over of disinfectants or microbes to succeeding samples by maintaining working levels of liquids in the containers to within prescribed limits so as to assure the cleaning of the stylus relative to a defined depth of immersion in the preceding cleaning or sample intake station. Containers are marked to identify the minimum required and maximum allowable levels, providing the basis for the timing and amount of liquid to be replenished. To minimize the frequency of replenishments, a digital (microprocessor implemented) control is used to avoid the use of excess liquids, beyond that needed to assure effective cleaning.

9 Claims, 6 Drawing Sheets

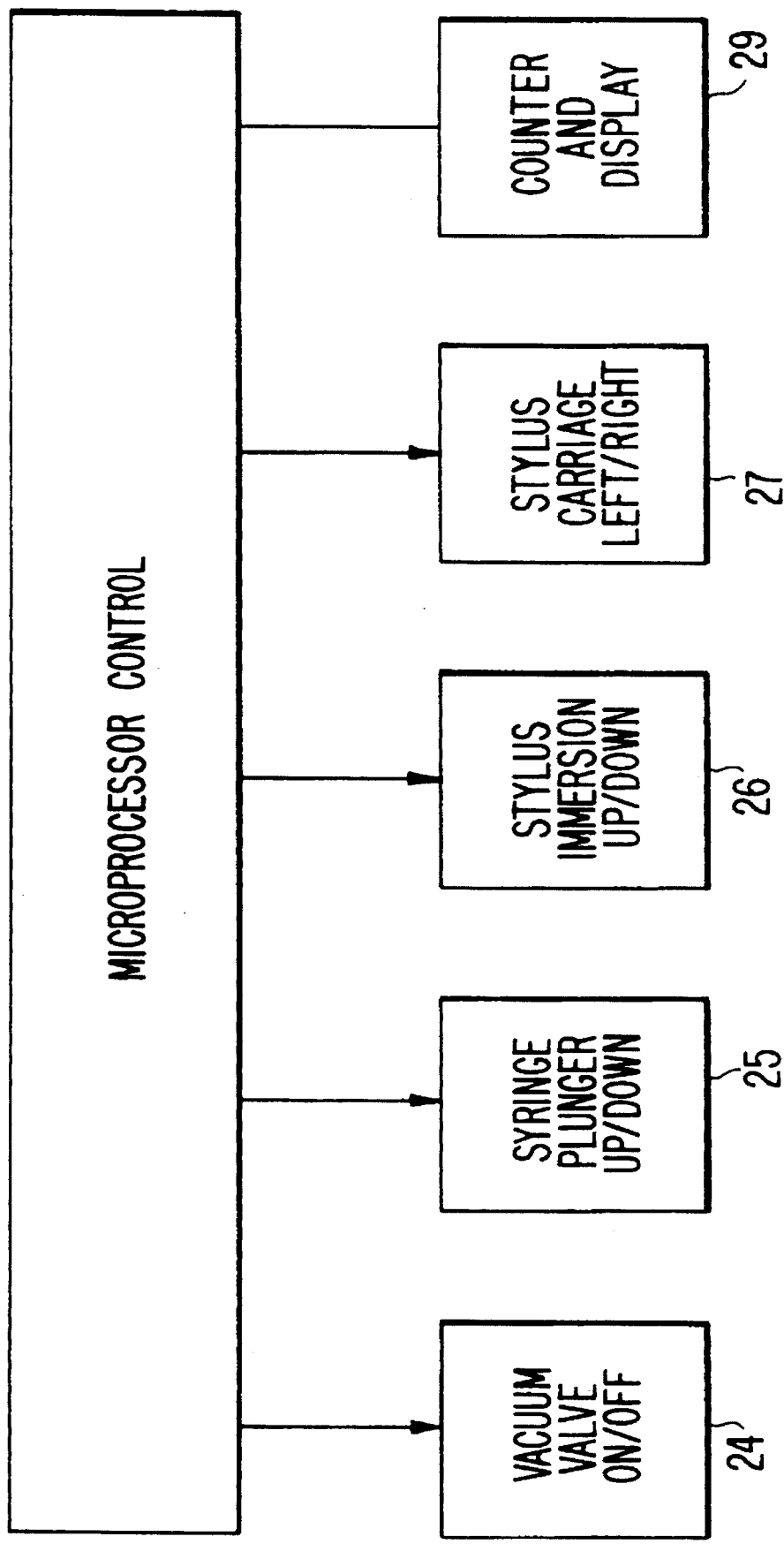

METHOD AND APPARATUS FOR CLEANING THE SAMPLE DELIVERY STYLUS OF MICROPROCESSOR CONTROLLED SPIRAL PLATERS

TECHNICAL FIELD

This invention relates to the cleaning of apparatus used to deposit microbe-containing solutions on agar plates by the spiral plating method.

BACKGROUND ART

Spiral platers are used to deposit microbe-containing liquid samples in a spiral pattern onto the surface of agar media contained in petri dishes. An essential part of such devices is a hollow stylus connected to a hollow plunger syringe, with an on-off valve mounted on top of the hollow plunger, further connected by tubing to a vacuum flask. With the valve open, the vacuum will draw liquid from the container into which the tip of the stylus is immersed, to fill the stylus tubing as well as the syringe. Simultaneous displacement of the syringe plunger, radial motion of the stylus tip riding on the surface of the agar, and rotation of the turntable holding the petri dish, deposit the microbe-containing sample in a spiral pattern and in amounts determined by the controlled rate of displacement of the syringe plunger. Earlier instrumentation of spiral platers utilize cam activation of plunger motion and manually controlled valve operation as well as manual movement of the stylus to and into sample and cleaning fluid containers. More recent spiral plater designs utilize microprocessor control of (1) plunger motion, (2) valve on-off activation and (3) automated motion of the stylus to a number of cleaning fluid containers, a sample holding container and immersion of the stylus into these containers. Such a microprocessor controlled spiral plater is sold by Spiral Biotech, Inc. of Bethesda, Md., as the AUTOPLATE Model 3000.

Practical utilization of the spiral plating method requires that (1) the stylus tubing holding the sample to be deposited is clear of any microbes from the previous sample and (2) that disinfectant used to clean the stylus prior to filling with the next sample is not carried over into this sample. The former would cause overestimation of the density of microbes in the sample under test while the latter would produce an underestimate by killing some or all of the microbes in the sample under test. The method used to avoid the above errors consists of opening the vacuum control valve and dipping the stylus a few times into and out of a container with disinfectant, such as a solution of sodium hypochlorite, followed by dipping the stylus a few times into and out of a cleaning solution, such as sterile water. The principal function of immersion into the disinfectant is to kill any microbes on the outer surface of the stylus tip. Multiple immersions into disinfectant and cleaning solutions serve to cause rapid, and sequential, flow of liquid and air—when the stylus is out of the liquid container—thereby scrubbing the inside of the stylus tubing to remove material from the previous sample.

Upon completion of the cleaning operation, the stylus tubing and syringe are allowed to fill with sterile water, preceding the intake of the next sample. In the earlier cam activated spiral platers, sample intake is also done by manually opening and then closing the vacuum valve; in the microprocessor controlled spiral plater, it is done automatically by activation of syringe plunger motion, with the vacuum valve closed.

Frequent manual operation of replenishing disinfectant and cleaning liquids is not consistent with the automated operation of microprocessor controlled spiral platers. Therefore, a method that cleans effectively and requires only occasional replenishing is highly desirable.

Liquid levels are important since, for example, allowing the liquid level to go below the immersion level of the stylus in a preceding container will likely cause carry over of microbes from the earlier sample and/or carry over of disinfectant into the next sample. In the AUTOPLATE Model 3000 this design requirement is addressed by seeking to continuously and automatically maintain a constant liquid level during operation. Specifically, a gravity syphon system is used in which liquid from an inverted container into an attached cup with upright openings is limited by atmospheric pressure on the free surface of the liquid. A vent tube is provided for the inverted container so that when liquid level in the associated open cup is lowered due to suction by the immersed stylus, air can pass into the inverted container reducing the partial vacuum in the container, thus allowing flow into the cup until the vent is again submerged below the liquid level in the cup. The liquid containing bottles, pressure equalization ports and associated manifolds to the stylus immersion openings add substantially to the cost of the instrument, since they must operate reliably—without leakage or significant change in liquid level—following repeated autoclaving to sterilize the assembly in the course of normal utilization, and because materials must be resistant to the corrosive effect of disinfectants such as sodium hypochlorite.

Disclosure of Invention

By maintaining the operating liquid level within a specified range, rather than requiring a fixed level to be continuously maintained, and by utilizing microprocessor (digital) control to minimize the amount of liquids used, this invention provides a less costly, more reliable and operationally more convenient method for avoiding carry over, without the need for frequent liquid replenishment, consistent with the automated operation of a microprocessor controlled spiral plater.

Containers, manufactured from an autoclavable material, are located at each of the stations where the stylus tip is to be immersed in a disinfectant and one or more cleaning liquids. Each container is marked with two lines, defining the minimum required liquid level $h_{min}$ and maximum allowable liquid level $h_{max}$ appropriate for the particular container. The minimum required liquid level $h_{min}$ is related to the maximum depth of immersion of the stylus tip in the preceding liquid container; in the case of the first cleaning station it relates to the maximum allowed immersion of the stylus into the preceding sample liquid during sample filling. The working liquid height $\Delta h$ is given by $$\Delta h = h_{max} - h_{min}. \qquad \text{Eq. 1}$$

The number n of available cleaning cycles before liquid replenishment is given by $$n = (A/V)\Delta h \qquad \text{Eq. 2}$$

where V is the cleaning volume of liquid needed for a single cleaning cycle and A is the surface area of the cleaning liquid in the container and n is a positive integer equal to at least one. The working volume $A\Delta h$ needed for a required number of cleaning cycles n without liquid replenishment can therefore be minimized by providing a large liquid surface area A and by minimizing the liquid volume V needed per cleaning cycle.

Maximizing the liquid surface area A becomes a part of the trade-offs in the physical design of the instrument. Minimizing the volume of liquid V used per cleaning cycle is accomplished by utilizing microprocessor control to (1) limit the length of time the stylus is immersed in the liquid with the vacuum valve open, or (2) by opening and closing the vacuum valve at selected times prior to, during and following immersion of the stylus into a cleaning liquid, or (3) by drawing a measured amount of liquid from the container, limited to that needed to assure effective cleaning, by microprocessor control of the syringe plunger with the vacuum valve closed: the amount of liquid drawn into the stylus tubing is then quantitatively defined by the distance travelled by the plunger and the cross-sectional area of the syringe. All of the above methods serve to avoid the intake of excess liquid, i.e. not needed to assure the prevention of disinfectant or microbe carry-over.

Purging of liquids from the stylus tubing and syringe is accomplished by opening the valve when the stylus is above the liquid level in the container, which flushes air through the stylus and syringe.

A method for disinfecting and/or cleaning the sample delivery stylus of a microprocessor controlled spiral plater to safeguard against carry-over of disinfectant or of microbes from a preceding sample into the following sample to be plated and requiring infrequent replenishment of cleaning or disinfecting liquids in accordance with the invention includes determining the minimum required liquid level $h_{min}$ in a container relative to the maximum expected depth of stylus immersion in the preceding cleaning, disinfectant or sample container, determining the maximum allowable liquid level $h_{max}$ in a container by adding to the minimum required level $h_{min}$ an amount $\Delta h$ computed from the number n of required cleaning cycles without replenishing the liquid in the container multiplied by the liquid cleaning volume V needed to assure adequate cleaning or disinfection and divided by the liquid surface area A in the container. The invention further includes minimizing the rate of working liquid $\Delta h$ utilization during cleaning operations by microprocessor control of (1) the time of stylus immersion with the vacuum valve open or (2) the opening and closing of the vacuum valve while the stylus is immersed or (3) by syringe plunger motion with the vacuum valve closed so as to limit the intake of cleaning liquid from a container to that needed to assure effective cleaning of the stylus. The invention further includes marking each container to show the maximum allowable and minimum required liquid levels to be maintained during cleaning operations, filling each container with the intended cleaning or disinfecting liquid to the mark showing the required maximum allowable level $h_{max}$, and replenishing the liquid level when it is reduced to the mark defining the minimum required level $h_{min}$ by an amount not to exceed the mark defining the maximum allowable liquid level $h_{max}$. An added feature of this method includes tilting the container when the minimum required level is reached so as to raise the liquid level up to but not to exceed the maximum allowable level mark $h_{max}$ in the region where the stylus to be cleaned is immersed into the liquid at the expense of lowering the liquid level at the opposite end of the container, thereby reducing the frequency of liquid replenishment.

A preferred apparatus for cleaning the sample delivery stylus tubing of microprocessor (digitally) controlled spiral platers to prevent microbes or disinfectant present during the cleaning operation from being carried over into the next sample includes a liquid intake and delivery system consisting of stylus tubing connected to a hollow plunger syringe, one end of a vacuum on/off valve connected to an external end of the plunger of the hollow plunger syringe, a tubing connection between another end of the vacuum valve and a flask further connected to a vacuum pump, at least one liquid reservoir container marked to identify maximum allowable and minimum required levels of liquid cleaning or disinfecting solution, a microprocessor controlled prime mover, such as a stepping motor, for positioning the liquid intake and delivery tip of the stylus tubing at the cleaning and test sample liquid reservoir containers and for programmed immersion of a tip into and out of the liquid in a container to a predetermined depth between a minimum depth $h_{min}$ in the container relative to the maximum expected depth of stylus immersion in a preceding one of the containers and determining a maximum allowable level $h_{max}$ in the container by adding to the minimum required level $h_{min}$ an amount $\Delta h$ computed from the number n of required cleaning cycles without replenishing the liquid in the container multiplied by the liquid cleaning volume V needed to assure adequate cleaning or disinfection and divided by the liquid surface area A in the container, a microprocessor controlled element which may be a solenoid for turning the vacuum valve on or off, a microprocessor controlled-prime mover, such as a stepping motor, for moving the syringe plunger while the stylus tip is immersed in a container liquid with the vacuum valve closed to intake a predetermined volume of the liquid into the stylus tubing, and a microprocessor control for controlling timing and a sequence of stylus tip positioning, immersion, vacuum valve on/off control and syringe plunger motion to minimize an amount of excess cleaning or disinfecting liquid intake, beyond that needed to prevent microbe or disinfectant carry over, thereby maximizing a number of cleaning cycles from a container before the liquid level is depleted to the minimum required level, requiring liquid replenishment to restore it by an amount not to exceed the maximum allowable level.

BRIEF DESCRIPTION OF DRAWINGS

FIG. 6 is a block diagram of the microprocessor functions associated with this invention.

Like reference numerals identify like parts throughout the drawings.

BEST MODE FOR CARRYING OUT THE INVENTION

Figure 1A:
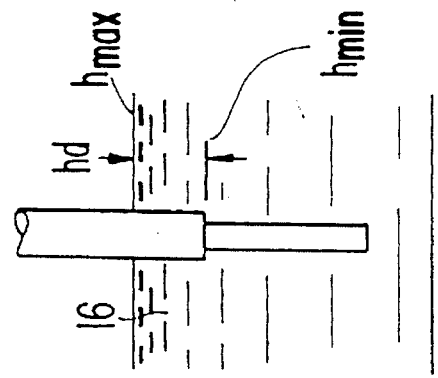
FIGS. 1A–D are illustrations of consecutive stylus immersion into a test sample, a disinfectant and two sterile water stations.
Figure 1B:
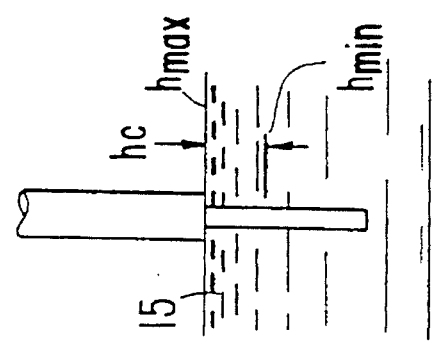
Figure 1C:
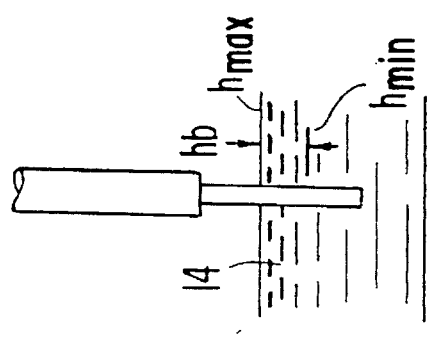

Referring to FIGS. 1A–D, it is a requirement of this invention to control the depth of the solutions at the sample (FIG. 1A), disinfectant (FIG. 1B) and two sterile water stations (FIGS. 1C and D). The positioning of the stylus at the sample, disinfectant, and sterile water stations is similar to the positioning performed by the AUTOPLATE Model 3000 but the actual methodology of immersion of the stylus tip 11 to the solution depths between the minimum and maximum levels illustrated in FIGS. 1A–D is an improvement over the operation of the AUTOPLATE Model 3000. The present invention, by using the sequence of solution immersions of FIGS. 1A–D, lessens consumption of disinfecting and cleaning solutions to reduce the need for frequent solution replenishment and increases reliability while reducing the cost of control of the solution levels at the disinfectant and sterile water stations when compared to the AUTOPLATE Model 3000.

With reference to FIG. 1A, it is a requirement of the present invention that the user limit the amount of sample placed in the sample filling container to a recommended height Ha shown. Microprocessor control of the motion of the stylus tip 11 then limits depth of immersion into the sample liquid 13 to a predetermined depth value ha. Since the stylus tubing which ends in tip 11 is generally flexible, it is encased into a section of rigid cylindrical tubing 12 which is manipulated by suitable drive mechanisms (not illustrated) to position the stylus at the stations of FIGS. 1A–D, as well as to lower it onto the agar surface and to provide the radial motion needed for spiral deposition.

The top level of the depth ha of FIG. 1A becomes the minimum required liquid level $hb_{min}$ in the first cleaning station of FIG. 1B. The cleaning station normally contains a disinfectant 14, such as a solution of sodium hypochlorite. The depth value of $hb_{max}$ is determined from the equation $\Delta h = h_{max} - h_{min}$, based upon knowledge of the liquid surface area Ab in the disinfectant station, the needed number nb of disinfection cycles without replenishment, and the volume amount of disinfectant Vb used per disinfection cycle.

The next cleaning station, illustrated in FIG. 1C, contains sterile water 15. To assure the removal of disinfectant from the stylus tip in this station, the minimum required surface level of sterile water $hc_{min}$ must be at least equal to the greatest depth of immersion of the stylus in the preceding disinfection station $hb_{max}$. The value of $hc_{max}$ is again determined by means of the equation $\Delta h = h_{max} - h_{min}$, but based upon the liquid surface area Ac in the first sterile water station, the needed number nc of sterile water cycles of the first sterile water station and the volume of sterile water Vc used per rinsing cycle.

Alternate liquid and air flow through the stylus tubing in the first sterile water station, and preferably also in the disinfectant station, is used to remove material of the preceding sample from the inside surface of the stylus tubing which will hold the next sample. Thus, the intake of the volume Vc is accomplished by means of a number of partial volumes and alternated with air flow.

Figure 1D:
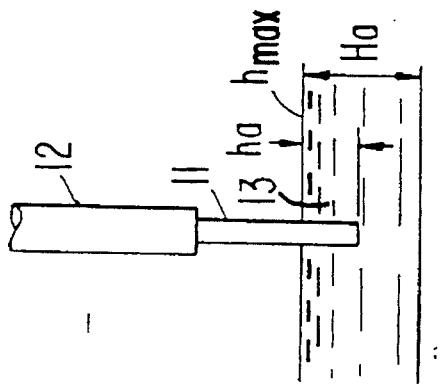
Figure 4:
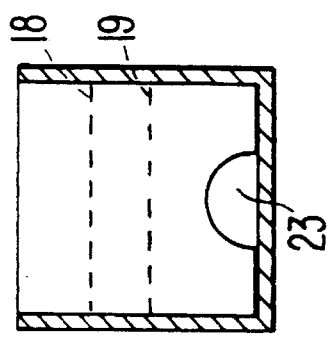
FIG. 4 is a sectional view of the liquid holding container of FIG. 2 taken along section line 4—4 including markings for maintaining required liquid levels.
Figure 5:
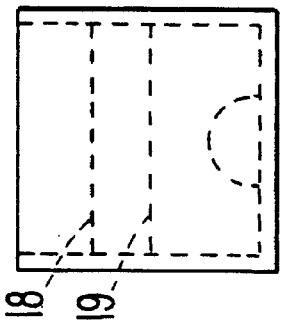
FIG. 5 is an end view of a liquid holding container of FIG. 3 including markings for maintaining required liquid levels.
Figure 2:
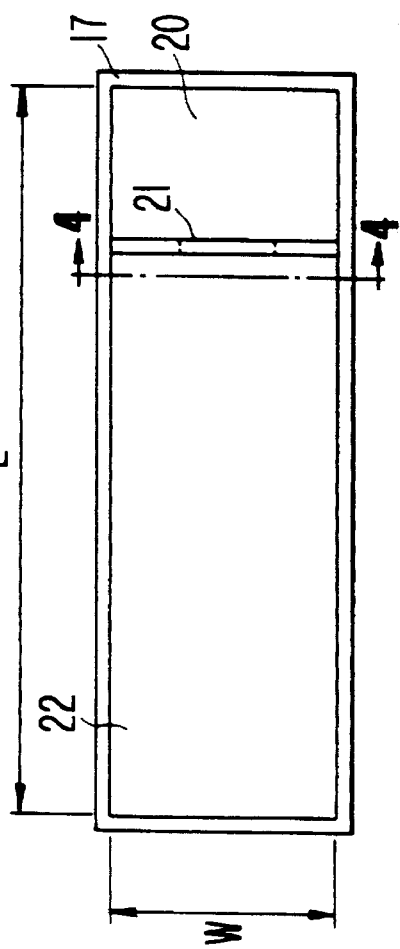
FIG. 2 is a top view of a liquid holding container having a separator of the working liquid volume from the liquid supply reservoir in accordance with the present invention.
Figure 3:
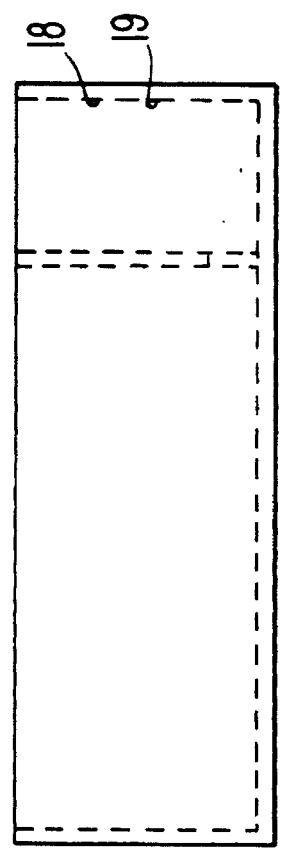
FIG. 3 is a front elevational view of a liquid holding container having the separator of the working liquid volume from the liquid supply reservoir in accordance with the present invention.

Since residual disinfectant, removed from the outside of the stylus tip, may be present in the first sterile water station, a second sterile water station is included as illustrated in FIG. 1D. Its principal function is to provide clean liquid 16 for filling the stylus tubing and syringe prior to intake of the next sample. Determination of $hd_{min}$ and $hd_{max}$ follows the same procedure described above for $hc_{min}$ and $hc_{max}$ using the equation $\Delta h = h_{max} - h_{min}$ with values Ad, nd and Vd which are analogous to the values used at the previous stations of FIGS. 1A–C.

FIGS. 2–5 show relevant features of the liquid holding containers for the three cleaning stations of FIG. 1B, 1C and 1D. The body of the container 17 is made of a material, such as polypropylene or glass, capable of withstanding repeated autoclaving and not subject to corrosion in the presence of disinfectants such as sodium hypochlorite. The simplicity of the structure of these containers also makes them amenable to the convenience of use as an expendable product. Each container includes markings of the maximum required liquid level $h_{max}$ 18 and minimum allowable liquid level $h_{min}$ 19 appropriate to the particular cleaning station. The liquid surface area A is the product L times W shown in FIG. 2. This area is separated by a divider 21 into a working volume 20, where stylus immersion takes place, and a supply reservoir 22. The benefit of the divider 21 is to minimize the likelihood of material removed in the cleaning process and subsequently present in the working volume 20 from mixing into the reservoir volume 22 thereby enhancing the probability that such removed material will be purged from the working volume as part of the liquid volume V drawn out by vacuum suction. The liquid level is maintained in the working volume 22 by virtue of pressure equalization provided by the cut-out 23 at the bottom of the divider 21.

FIG. 6 illustrates a block diagram of the microprocessor control functions of the vacuum valve, syringe plunger, stylus immersion and stylus carriage which may be used with the practice of the present invention. The block labelled "microprocessor control" preferably represents the microprocessor control of the AUTOPLATE Model 3000 and the blocks 24-27, respectively labelled vacuum valve on/off, syringe plunger up/down, stylus immersion up/down and stylus carriage left/right represent controls present in the AUTOPLATE Model 3000. The syringe plunger, stylus immersion and stylus carriage functions may be driven by stepping motors which directly interface with the microprocessor (digital) control. The vacuum valve may be a solenoid controlled valve. The counter and display 29 keeps track of the number of cleaning cycles executed in any one container and a display of a warning signal indicating that liquid replenishment in the container is required.

Reduction of the cleaning volume of disinfectant is preferably accomplished by a measured intake of disinfectant utilizing syringe plunger action. Since cleaning normally is done after completion of plating, the stylus tubing and syringe remain filled with liquid—sterile water plus the remaining sample—and the plunger had been lowered by at least the amount needed to plate the sample. The plunger can therefore be raised while the stylus tip is immersed in the disinfectant (with the vacuum valve remaining closed) to intake a fixed amount of disinfectant. A delay can then be provided, to assure good contact of the disinfectant with any microbes on the outside of the stylus tip and inside the stylus tubing, before raising the plunger to its highest position, lifting the stylus out of the disinfectant container and opening the vacuum valve to flush out the remainder of the previous sample and to allow the disinfectant to clean the tubing and syringe. These functions are illustrated by blocks 24-26 of FIG. 6 as described above.

Minimizing the liquid volume per cleaning cycle in the two sterile water stations of FIGS. 1C and 1D is preferably done by closing the vacuum valve function 24 of FIG. 6 before immersion into the sterile water and opening it at a selected time prior to lifting the stylus out of the liquid as represented by stylus immersion function 26 of FIG. 6 so as to assure the intake of the amount of sterile water per immersion needed to assure effective cleaning.

Figure 7A:
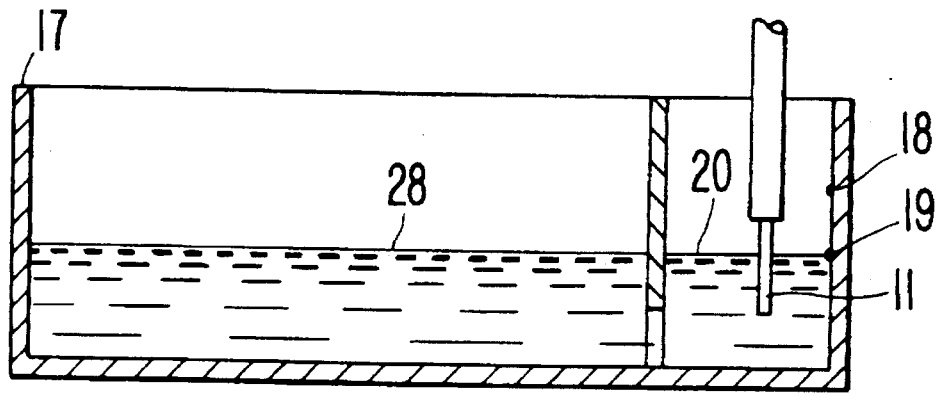
FIG. 7A and B illustrate tilting of the container illustrated in FIGS. 2–5 to recover liquid working level without liquid replenishment.
Figure 7B:
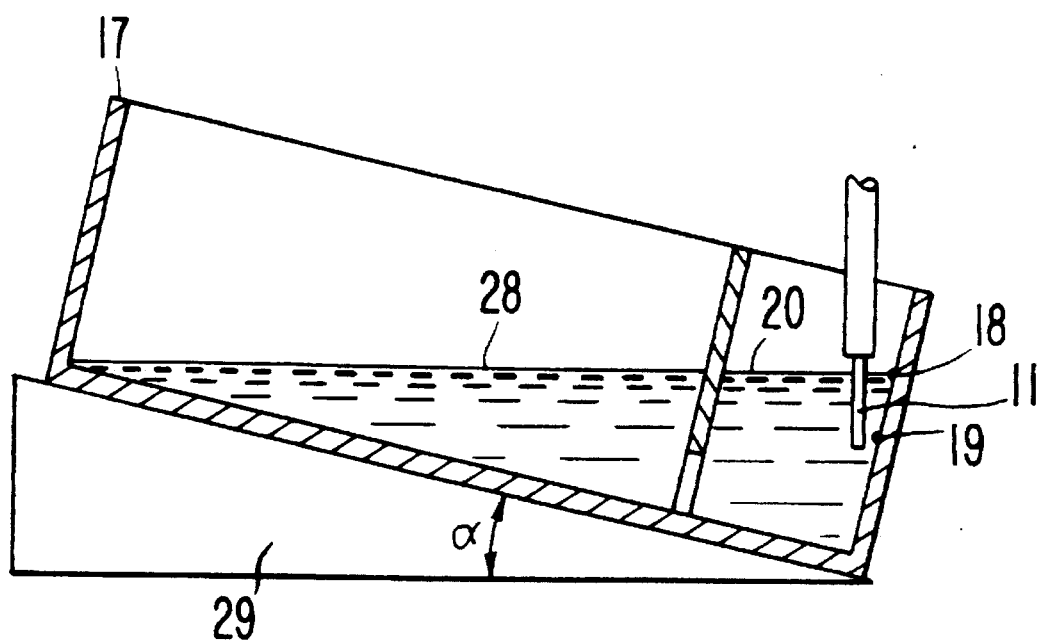

FIGS. 7A and B illustrate a technique to recover a maximum amount of working liquid at the stations of FIGS. 1A–D without liquid replenishment. The container 17 in FIG. 7A represents the liquid within any of the stations of FIGS. 1A–D described above and below in FIG. 9 with the container bottom being in a horizontal orientation in which the liquid level relative to the bottom of the container is identical in the working volume 20 and supply reservoir 22. In FIG. 7B a triangular shim 29 is inserted to incline the container 17 from its horizontal orientation of FIG. 7A to increase the depth of liquid in working volume 20 to permit use of the working fluid without replenishment by again positioning the surface level of the liquid above the minimum level 19 of FIG. 7A. As can be seen, the shim 29 may be inserted underneath the individual containers of FIGS. 1A–D and FIG. 9 as described below to raise the level of the working fluid at each of the stations above minimum level 19 up to the maximum level 18 without replenishment. Furthermore, more than one shim each having a different angle of inclination $\alpha$ may be used at each station to facilitate the use of the maximum amount of working fluid without replenishment.

Figure 8:
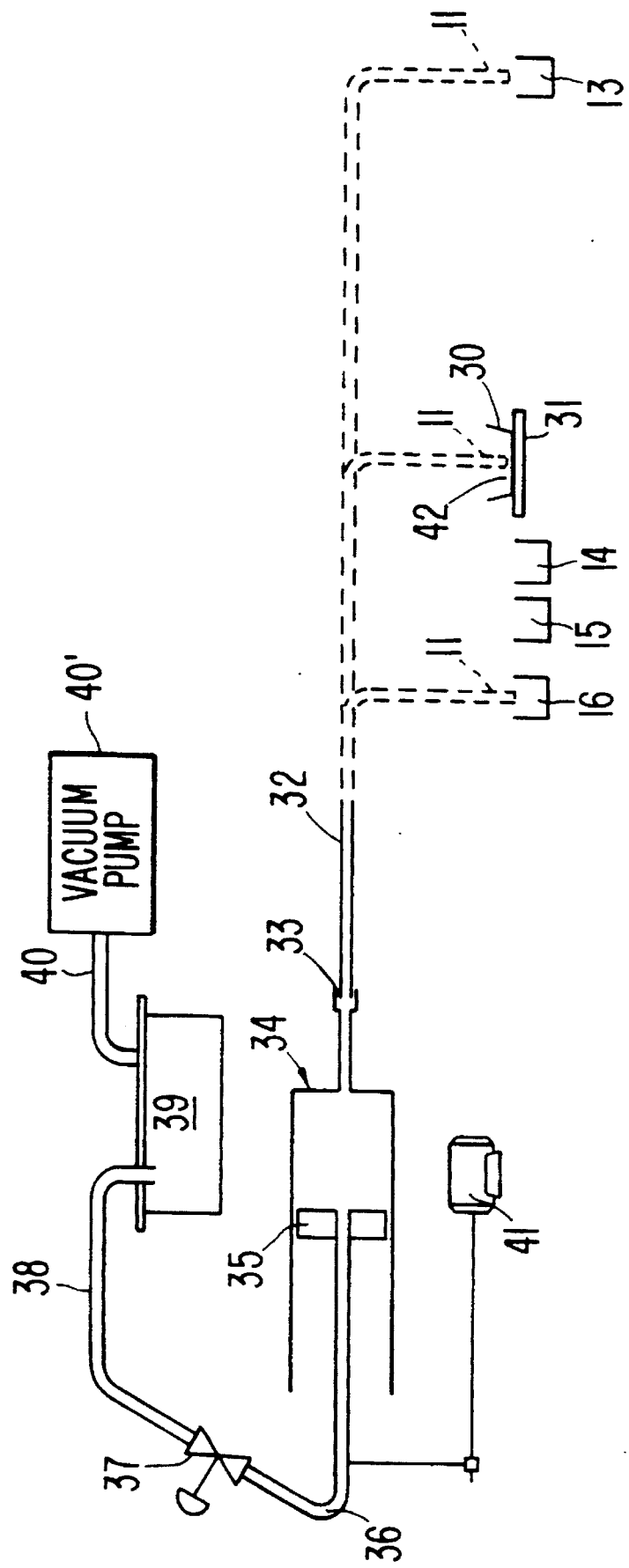
FIG. 8 is a schematic diagram of the liquid intake and delivery system of a prior art spiral plater which has been modified to practice the present invention.
Figure 9:
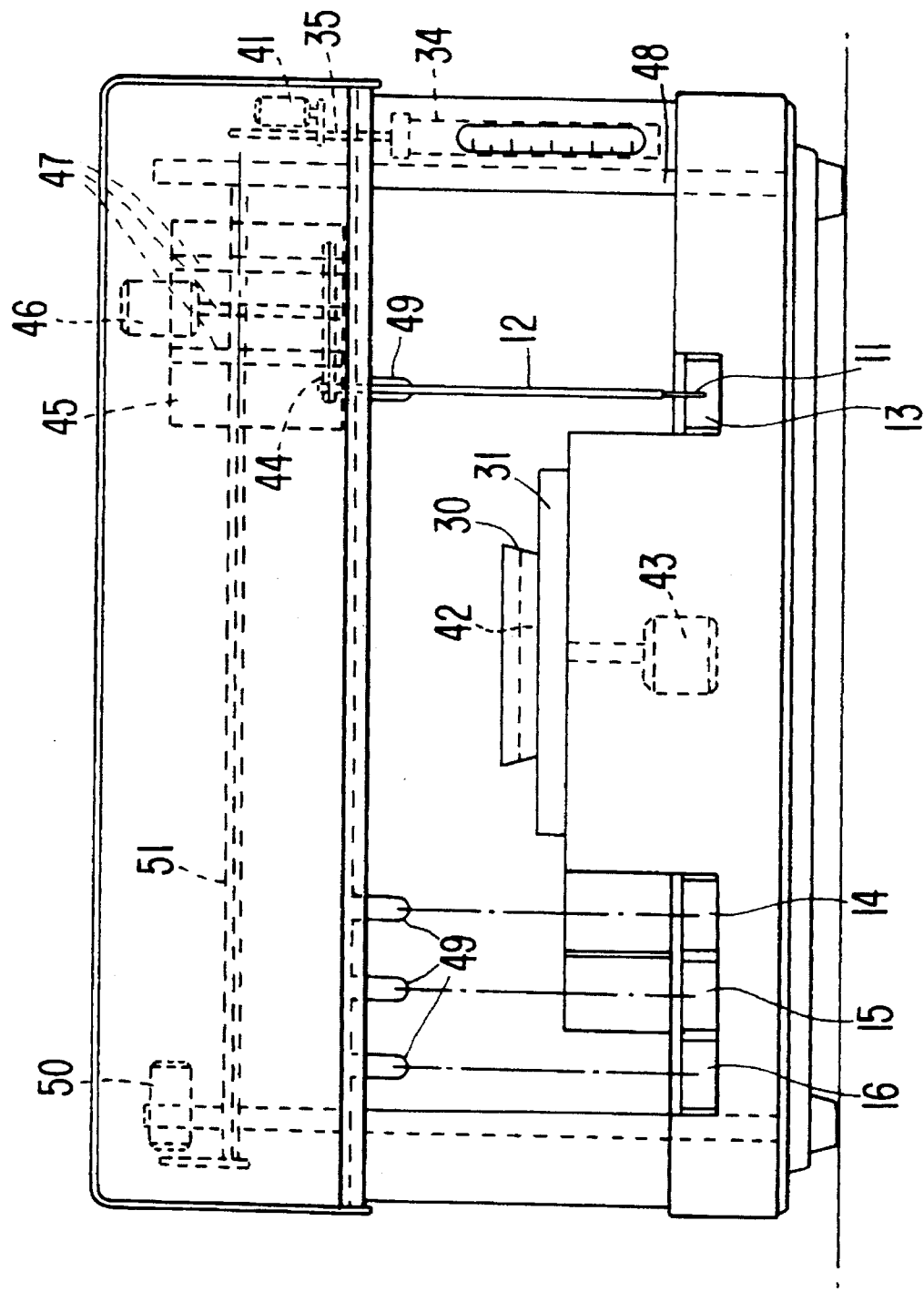
FIG. 9 is a schematic front view of a prior art microprocessor controlled spiral plater which has been modified to practice the present invention.

FIGS. 8 and 9 illustrate the preferred apparatus of the invention. The apparatus of FIGS. 8 and 9 is representative of the AUTOPLATE Model 3000 and is also disclosed in PCT application number PCT NL93/00110. The function of the apparatus of the AUTOPLATE Model 3000 and that disclosed in the PCT NL93/00110 has been modified in function to perform the stylus immersion functions described above in conjunction with the stations of FIGS. 1A–D.

In the schematic representation of the liquid intake and delivery apparatus of FIG. 8, the tip 11 of the stylus tubing 32 is alternately placed in sample liquid 13, disinfectant 14, sterile water 15 and 16, or onto the surface of the agar 42 in petri dish 30 located on turntable 31. The stylus tubing 32 is joined to the output end of syringe 34 by means of vacuum tight connection 33. The hollow plunger 35 of syringe 34 is connected to vacuum valve 37 which is then connected by tubing 38 to flask 39. Tubing 40 is connected to a vacuum pump 40', serving to create and maintain a vacuum in flask 39. When the vacuum valve 37 is in the open position and the stylus tip 11 is immersed in a liquid, the vacuum will draw the liquid into the stylus tubing, syringe body and hollow plunger, and expel it into the flask. When the stylus tip is exposed to the air, any residual liquid in the system will be drawn by vacuum into the flask. Microprocessor actuated stepping motor 41 serves to move the syringe plunger 35 in the body of syringe 34 in accordance with the syringe plunger control 25 of FIG. 6. With the vacuum valve 37 closed, the plunger 35 is moved left and right (up and down in the AUTOPLATE 3000) to respectively intake and expel liquids.

FIG. 9 illustrates the physical arrangement of the preferred apparatus of the invention. Slots 49 in the front cover provide clearance for the motions of the stylus tubing, which is enclosed in rigid support tubing 12 for purposes of manipulation of the stylus tip 11, into the sample liquid 13, disinfectant 14 and the cleaning liquids 15 and 16. The sample and cleaning containers are preferably separated by the turntable 31 and its drive stepping motor 43 assembly. The microprocessor control of FIG. 6 is contained within the arrangement of FIG. 9. Rotation and transport of the stylus tubing is accomplished by pivoting the support tubing 12 about the rotary shaft 44 mounted on the carriage 45 which is moved to the sample filling location 11, and the three cleaning locations 14, 15 and 16 and plating on the agar 42 by means of the microprocessor controlled stepping motor 50 and the lead screw 51. The microprocessor controlled stepping motor 46 serves to both rotate the stylus tubing support 12 as well as to move it vertically up and down by means of the linear guides 47. The stylus tubing is connected (not shown in FIG. 9) to the bottom of syringe 34 which is mounted to frame 48. The microprocessor controlled stepping motor 41 serves to drive syringe plunger 35 up or down.

A preferred apparatus for holding cleaning liquids is as illustrated in FIGS. 2–5 and described above, including the addition of a separator 21 to reduce the mixing of liquid from the working region into the reservoir region. Although not shown in FIGS. 2–5, each cleaning container 17 of the preferred apparatus is provided with a cover to prevent airborne contaminants from falling into the cleaning liquid while the system is not in use. For cleaning operation, the cover is moved to allow the stylus to enter the working area but keeping the reservoir area covered.

While the invention has been described in terms of its preferred embodiment, it should be understood that numerous modifications may be made thereto without departing from the spirit and scope of the appended claims. It is intended that all such modifications fall within the scope of the appended claims.

We claim:

1. A method for at least one of disinfecting or cleaning a sample delivery stylus of a digitally controlled spiral plater to safeguard against carry-over of disinfectant into a next sample to be plated or carry-over of microbes from a preceding sample into a next sample to be plated while minimizing replenishment of cleaning or disinfecting liquids comprising:

(a) determining a required minimum level $h_{min}$ of a cleaning or disinfecting liquid in at least one container relative to a maximum expected depth of immersion of a sample delivery stylus in a preceding container with the minimum level providing for immersion of the sample delivery stylus to at least a depth of immersion in the preceding container in which the sample delivery stylus was last immersed;

(b) determining a maximum allowable level $h_{max}$ of the cleaning or disinfection liquid in the at least one container by adding to the required minimum level $h_{min}$ in the at least one container an amount $\Delta h$ of the liquid computed from a positive integer number n, equal to at least one, which represents the required number of cleaning cycles or disinfecting cycles without replenishing the liquid in the at least one container, multiplied by a liquid cleaning volume V needed to assure cleaning or disinfecting of the sample delivery stylus and divided by a surface area A of the liquid in the at least one container;

(c) controlling, with a digital control, intake of a volume of the liquid from the at least one container into the sample delivery stylus to minimize a rate of consumption of the liquid in the at least one container;

(d) marking the at least one container with the maximum allowable and minimum required liquid levels $h_{max}$ and $h_{min}$ respectively to be maintained during at least one of a disinfecting or cleaning operation;

(e) filling the at least one container with the liquid to a level between the marks identifying the maximum and minimum allowable levels $h_{max}$ and $h_{min}$; and (f) replenishing the liquid within the at least one container when reduced to the mark of the minimum level $h_{min}$ by an amount not to exceed the mark of the maximum allowable level $h_{max}$.

2. A method in accordance with claim 1 wherein:

minimizing a rate of consumption of the liquid during the at least one disinfecting or cleaning operation comprises using the digital control to control a length of time of immersion of a tip of the sample delivery stylus in the liquid with a vacuum valve continuously in the open position.

3. A method in accordance with claim 1 wherein:

minimizing a rate of consumption of the liquid Ah during the at least one disinfecting or cleaning operation comprises using the digital control to control opening and closing of a vacuum valve while a tip of the sample delivery stylus is immersed into and out of the liquid.

4. A method in accordance with claim 1 wherein:

minimizing a rate of consumption of the liquid during the at least one cleaning or disinfecting operation is performed by using the digital control to control motion of a syringe plunger with a vacuum valve closed to limit intake of the liquid from the at least one container to an amount of the liquid required for cleaning or disinfecting of the sample delivery stylus.

5. A method in accordance with claim 1 wherein:

a frequency of replenishing the liquid is reduced by tilting the at least one container when the minimum required level $h_{min}$ is reached therein so as to raise a liquid level in the at least one container up to but not to exceed the maximum allowable level mark $h_{max}$ in a region of a surface of the liquid where the sample delivery stylus is to be immersed while lowering a level of the liquid at an opposite end of the at least one container.

6. An apparatus for at least one of disinfecting or cleaning a sample delivery stylus of a digitally controlled spiral plater to safeguard against carry-over of disinfectant into a next sample to be plated or carry-over of microbes from a preceding sample into a next sample to be plated while minimizing replenishment of cleaning or disinfecting liquids comprising:

(a) a liquid intake and delivery system comprising a delivery stylus connected to a hollow syringe having a plunger, a vacuum on/off valve connected to an external end of the plunger of the hollow syringe, a tubing connection at the other end of the vacuum on/off valve a flask at the opposite end of the tubing connection and a vacuum pump connected to the flask;

(b) a test-sample container for containing a test sample and at least one liquid reservoir container marked to identify a maximum allowable and a minimum required level of cleaning or disinfecting liquid to be contained therein, the minimum required level $h_{min}$ of the liquid in the at least one liquid reservoir container providing for immersion of the delivery stylus to at least a depth of immersion in an immediately preceding container in which the delivery stylus was last immersed and the maximum allowable level being determined by adding to the minimum required level of the liquid in the at least one liquid reservoir container an amount $\Delta h$ of the liquid computed from a number n of required cleaning cycles or disinfecting cycles without replenishing the liquid in the at least one liquid reservoir container multiplied by a cleaning volume V of the liquid needed to assure cleaning or disinfecting of the delivery stylus and divided by a liquid area A in the at least one liquid reservoir container, with n being a positive integer equal to at least one;

(c) a digitally controlled prime mover for positioning a delivery tip of the delivery stylus in the test-sample container and in the at least one liquid reservoir container and for programmed immersion of the delivery tip into and out of the liquid in the containers to a predetermined depth;

(d) a digitally controlled prime mover for moving the plunger of the hollow syringe while the delivery tip is immersed in one of the test-sample container and the at least one liquid reservoir container with the vacuum on/off valve closed to intake a predetermined volume of liquid into the delivery stylus; and (e) a digital control for controlling the prime movers and the vacuum on/off valve to provide controlled timing and a sequence of positioning and immersion of the delivery tip and to provide controlled motion of the plunger to minimize consumption of an amount of the cleaning or disinfecting liquid beyond that needed to prevent microbe carry-over or disinfectant carry-over in the delivery stylus, thereby maximizing the number n of cleaning or disinfecting cycles from the at least one liquid reservoir container before the level of the liquid therein is depleted to the minimum required level $h_{min}$ of the liquid requiring liquid replenishment to restore the liquid level by an amount not to exceed the maximum allowable liquid level $h_{max}$.

7. An apparatus in accordance with claim 6 further comprising:

a partition positioned in the at least one liquid reservoir container to provide separation of a surface region of the liquid into which the delivery stylus is immersed from a remaining surface region of the liquid in the at least one liquid reservoir container so as to reduce mixing of two liquid volumes within the two surface regions while maintaining a common liquid level in the two surface regions.

8. An apparatus in accordance with claim 6 further comprising:

a mechanism for tilting the at least one liquid reservoir container to raise a liquid level therein up to but not to exceed the maximum allowable liquid level mark $h_{max}$ in a region where the delivery stylus is to be immersed into the liquid while lowering a liquid level at an opposite end of the at least one liquid reservoir container thereby reducing a frequency of liquid replenishment when the minimum required liquid level mark $h_{min}$ is reached.

9. An apparatus in accordance with claim 6 further comprising:

a counter for counting a number of cleaning or disinfecting cycles performed in the at least one liquid reservoir container and a display warning a user when a number of available cleaning or disinfecting cycles without liquid replenishment has been reached.

* * * * *